United States Patent [19]
Burkhead

[11] Patent Number: 5,334,132
[45] Date of Patent: Aug. 2, 1994

[54] CONVERTIBLE ARM SLING

[76] Inventor: Wayne Z. Burkhead, 2909 Lemmon Ave., Dallas, Tex. 75204

[21] Appl. No.: 49,986

[22] Filed: Apr. 16, 1993

[51] Int. Cl.⁵ .............................................. A61F 5/40
[52] U.S. Cl. ............................................. 602/4
[58] Field of Search ............... 602/4, 20, 21; 128/874, 128/875, 876, 878; 2/16, 17, 158

[56] References Cited

U.S. PATENT DOCUMENTS

| | | | |
|---|---|---|---|
| 2,594,809 | 4/1952 | Sanders | 602/4 |
| 3,788,308 | 1/1974 | Simpson | 602/4 |
| 3,815,588 | 6/1974 | Klausner | 128/77 |
| 4,285,337 | 8/1981 | Cosentino | 128/133 |
| 4,327,909 | 5/1982 | Neufeld | 272/137 |
| 4,359,784 | 11/1982 | Harrington | 2/158 X |
| 4,372,301 | 2/1983 | Hubbard et al. | 128/94 |
| 4,510,928 | 4/1985 | Ackley | 128/87 R |
| 4,617,923 | 10/1986 | Coleman | 128/94 |
| 4,622,961 | 11/1986 | Christensen | 128/94 |
| 4,754,498 | 7/1988 | Stinemates | 2/17 |
| 4,759,353 | 7/1988 | Melendez et al. | 128/94 |

Primary Examiner—Richard J. Apley
Assistant Examiner—Beverly A. Meindl
Attorney, Agent, or Firm—Dennis T. Griggs

[57] ABSTRACT

An improved arm sling includes a forearm support section having a resealable opening in a bottom panel for permitting exercise, flexure and extension of a patient's forearm without removing the sling harness from the patient. A splint pocket is also provided for housing a removable splint for supporting the patient's hand in a neutral position. An external pocket encloses a foam cushion for conforming engagement with the patient's waist, thus providing an abduction effect.

10 Claims, 3 Drawing Sheets

CONVERTIBLE ARM SLING

FIELD OF THE INVENTION

This invention relates generally to orthopedic devices for supporting limbs of patients, and in particular to an arm sling which provides features for exercise therapy, comfort, and ease of use.

BACKGROUND OF THE INVENTION

An important part of the medical treatment of an arm injury consists of post-operative support of the arm of the injured person, usually accomplished by means of a simple sling. Such injuries typically involve bone fractures and strain, tearing or rupture of one or more connective ligaments. After reduction of the fracture and repair of ligaments, the injury is treated by supporting the forearm in a slightly elevated, retracted position.

Arm slings are employed for supporting the forearm of a patient who suffers from an injury or disability for the purpose of restricting the normal manipulation of the arm. The restraining effect of the sling promotes healing since the limb is immobilized and the bone and tissues have an opportunity to heal.

Such treatment may be required in order to allow healing of the arm or wrist after surgery, or simply to allow natural healing by removing stress from the injured limb. Healing may occur through the recession of inflammation, for instance, or through the regeneration of bone or muscle tissues after a broken bone is set or after surgical correction of a physical disfunction. Examples of such disfunction are traumatized or arthritic joints or traumatized soft tissues.

DESCRIPTION OF THE PRIOR ART

The traditional sling is a square or rectangular section of cloth that is folded to form a pocket for supporting the injured limb. The ends of the folded cloth are pulled around the patient's neck and tied in a knot. In this arrangement, the sling is suspended from the patient's neck for supporting the injured limb. Improvements for support have been made by adding a waist belt which further secures the sling against the patient's body. While the iramobilization that the sling provides may result in healing, it may also have a debilitating effect on the joints and muscles causing stiffness and loss of extension range.

Some rehabilitation therapy involves occasional flexing of the limb in order to avoid stiffness or atrophy. Conventional slings must be removed to permit the forearm to be flexed and exercised.

In an improved technique, a resilient sling has been proposed which allows the user to flex the arm muscles by asserting a force to stretch the sling. A limitation on the use of that technique is that it requires the patient to exert a force against the resilient restraint and may result in reinjuring the broken limb.

Another limitation on the use of conventional slings is that the positioning of the forearm against the torso is uncomfortable. Moreover, presently available slings do not provide wrist support so that the hand is maintained in a neutral position, desirable when the patient is sleeping.

Accordingly, it will be appreciated that an improved sling is needed which allows the patent to easily disengage the forearm to flex and straighten out the elbow without removing or adjusting the entire sling. There is also a need for an improved sling which provides an abduction pillow effect so that the placement of the forearm against the torso provides a comfortable fit. For some injuries, for example wrist fractures, there is a need for an improved sling which provides wrist support to maintain the patient's hand in a neutral position so that the wrist remains unstressed, especially while the patient is asleep.

SUMMARY OF THE INVENTION

The present invention provides an improved sling which includes a reclosable bottom opening to permit the patient's forearm to be flexed without removing the sling. The sling further provides a removable splint for holding the patient's hand in a neutral position so that the patient does not stress the wrist joint. According to another aspect of the present invention, the sling includes an inner pouch in which a foam cushion provides an abduction pillow effect.

ADVANTAGES OF THE INVENTION

One advantage of the present invention is that the patient may flex the forearm by simply opening the bottom panel of the sling and extending the forearm downwardly without removing or disassembling the sling harness. Another advantage is that the patient may maintain the hand in a neutral position with the aid of a removable splint. Yet another advantage of the present invention is that an abduction cushion may be removably inserted in an external pouch for engagement with the patient's hip so that a comfortable fit is maintained between the arm and the patient's body.

The construction and features of the present invention will be understood by one skilled in the art after reading the following description with reference to the attached drawings.

BRIEF DESCRIPTION OF THE DRAWINGS

Referring now to the drawings in which like reference numerals and letters indicate corresponding elements throughout the several views.

DETAILED DESCRIPTION OF THE PREFERRED EMBODIMENT

Figures 1, 2, 3:
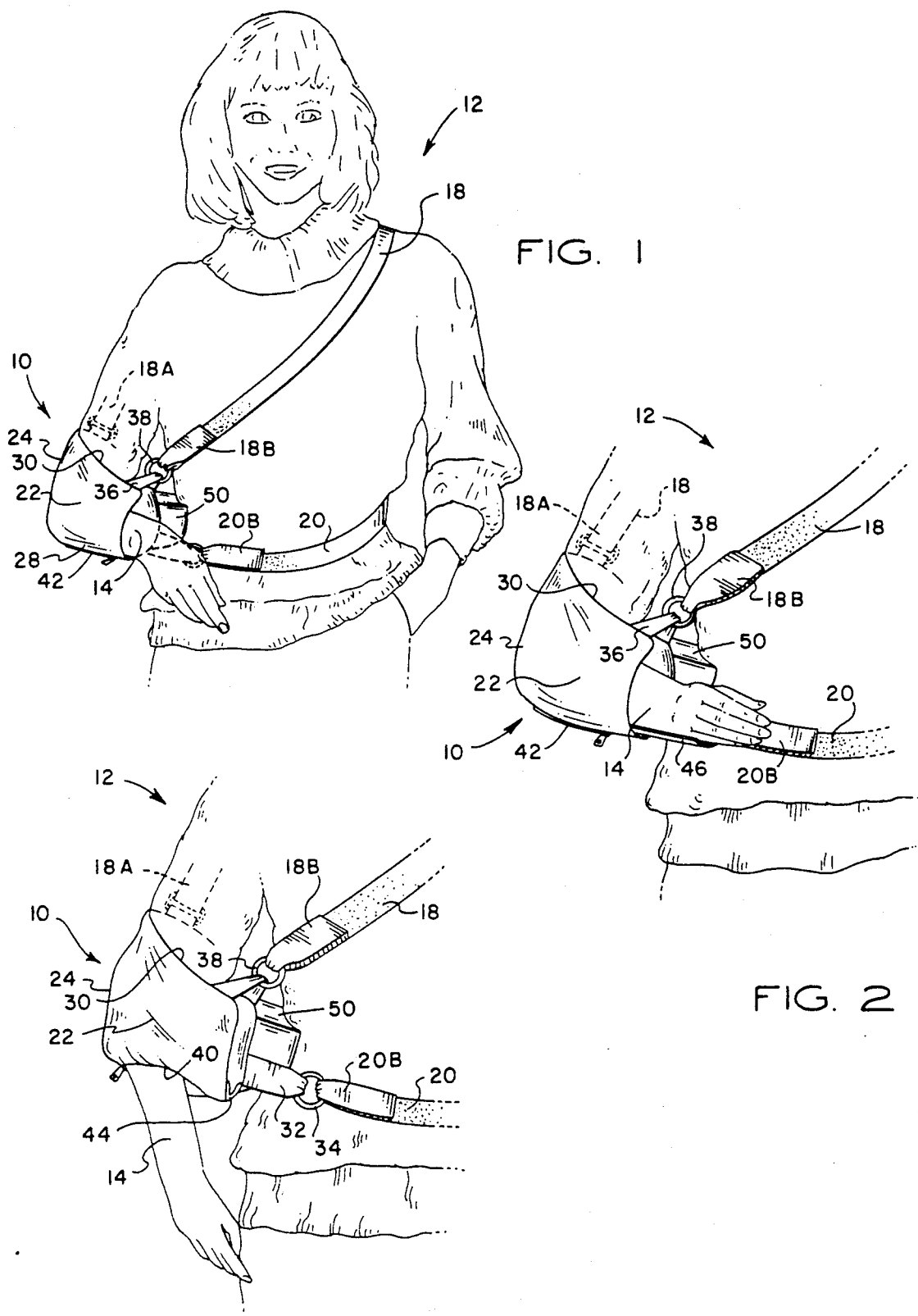
FIG. 1 is a perspective view of an improved arm sling constructed in accordance with the principles of the present invention.
FIG. 2 is a perspective view of the arm sling of FIG. 1 with a removable splint installed.
FIG. 3 is a perspective view of the arm sling of FIG. 1 with the patient's forearm extended through an opening in the sling to permit exercise therapy.

In the description which follows, like parts are marked throughout the specification and drawings with the same reference numerals, respectively. The drawing figures are not necessarily drawn to scale and the proportions of certain parts have been exaggerated for purposes of clarity.

Referring now to FIG. 1, an improved sling 10 according to the present invention is being worn by a patient 12. As can be seen from the silhouette in FIG. 3, the forearm 14 is easily disengaged from the sling 10 by opening a resealable opening 16 in the bottom of the sling 10. The sling 10 is supported around the patient's shoulder by a shoulder strap 18 and around the patient's waist by a waist strap 20.

Reference is now made to FIGS. 4–9 which show various aspects of the sling 10. The sling 10 includes a trough-like forearm section 22 preferably made of cloth fabric or other washable material. The forearm section 22 is defined by an inside panel 22A, an outside panel 22B an elbow portion 24, a wrist portion 26, a bottom panel 28, and an open top 30. The waist strap 20 has a first end 20A coupled to the mid portion of the elbow end 24 of the forearm section 22. A second end 20B of the waist strap 20 is adjustably and removably attached to the wrist portion 26 via a wrist strap 32. The second end 20B of waist strap 20 has disposed on its upper and lower surface hook and loop VELCRO ® fasteners for adjusting the waist strap 20 around the patient's waist. The wrist strap 32 is attached near the wrist end 24 by a plastic coupling ring 34.

The shoulder strap 18 has a first end 18A attached to the border of the open top section 30 near the elbow portion 24 and a second end 18B attached to the top section 30 near the wrist end loop 32. The second end has VELCRO ® hook and loop material disposed on its upper and lower surfaces respectively, for adjustable coupling to a wrist strap 36 and a coupling ring 38.

Referring to FIG. 3, the bottom panel 28 is intersected by a resealable opening 40 which extends from the elbow portion 24 to a point near the wrist portion 26. It should be understood that the resealable opening 40 does not extend completely through to the wrist portion, thus permitting the patient to extend her arm for exercise therapy, examination or treatment without removing the straps. In the preferred embodiment, the opening 40 is releasably closed by a zipper 42. It should be understood that other resealable openings such as hook and loop fasteners or buttons and the like may be employed without departing from the scope of the present invention.

Figure 4:
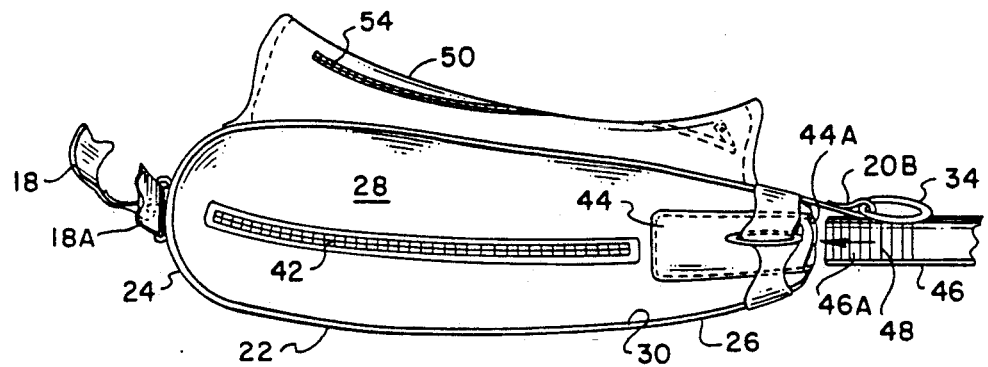
FIG. 4 is a top plan view thereof.
Figure 5:
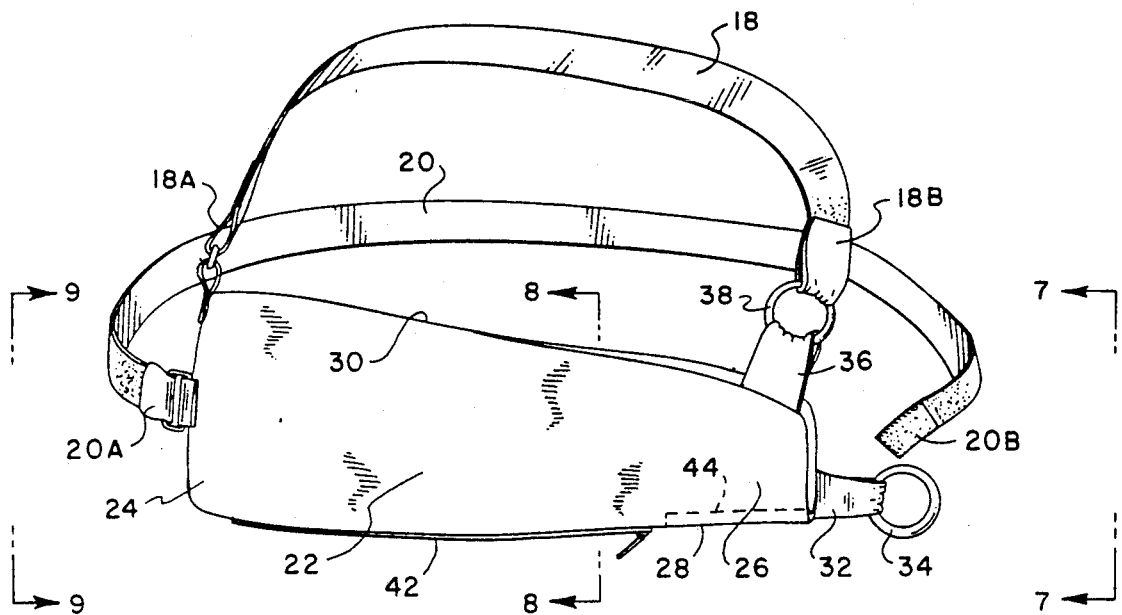
FIG. 5 is a side elevational view thereof.
Figure 7:
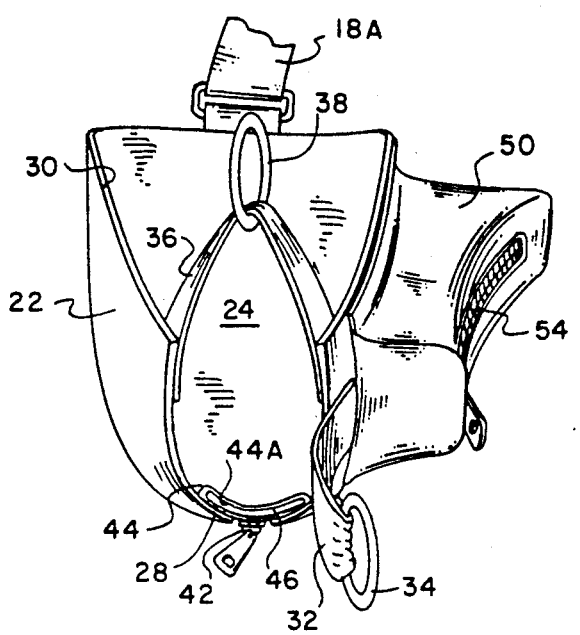
FIG. 7 is a front elevational view thereof.

Referring now to FIG. 2, FIG. 4 and FIG. 7, a small pocket 44 is attached to a bottom panel portion of the wrist portion 26 for receiving a splint 46. The splint 46 is removable and is utilized for keeping the patient's hand in a neutral position, typically at night when the patient is sleeping, so that the wrist is not stressed. Preferably, the pocket 44 has a chamber 46 (FIG. 7) which is dimensioned for a sliding fit with the splint 46. Additionally, the insertion end portion 46A is provided with a covering 48 of hook or loop fasteners, and the facing inside surface 44A of the pocket is fitted with mating hook or loop fasteners 48, the splint 46 is securely retained within the pocket cavity 44A upon full insertion.

Figure 6:
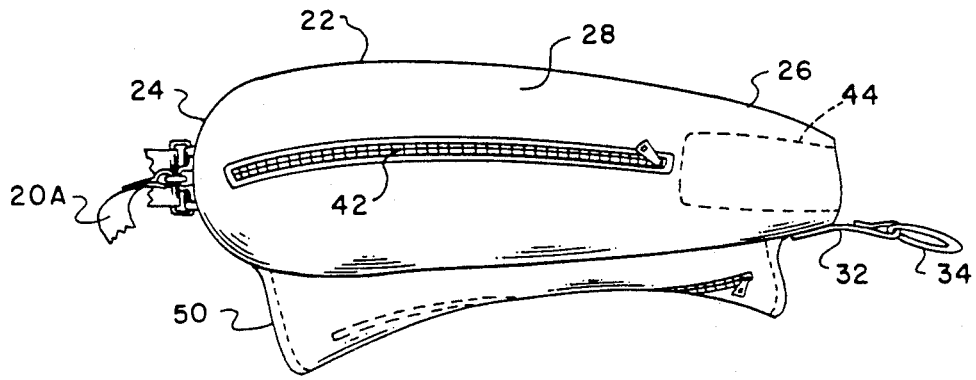
FIG. 6 is a bottom plan view thereof.
Figure 8:
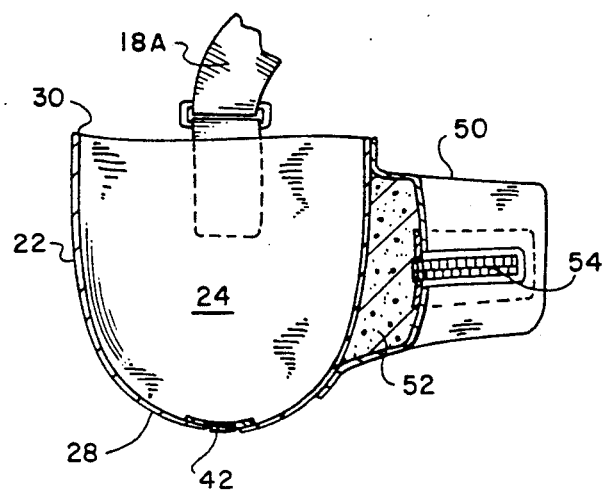
FIG. 8 is a sectional view thereof taken along the line 8—8 of FIG. 5.
Figure 9:
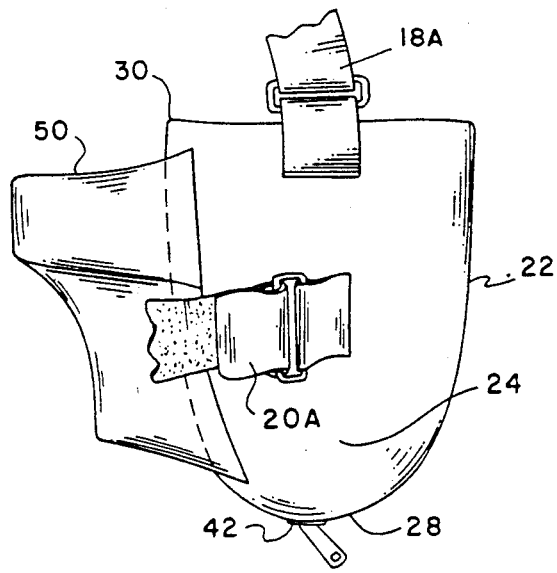
FIG. 9 is a rear elevational view thereof, taken along the line 9—9 of FIG. 5.

Referring now to FIGS. 6, 7, 8 and 9, the sling 10 is provided with an external pouch 50 for receiving a cushion 52 (FIG. 8) engageable with the patient's hip the pouch 50 is secured to the external side surface of the inside panel member 22A, as shown in FIG. 4, FIG. 6 and FIG. 8. The pouch 50 includes a zipper 54 for securing the cushion within the pouch 50. The zipper 54 is located on the inner side of the pouch engaged against the patient's hip. It should be understood however, that the zipper 54 may be positioned on the bottom or top of the pouch 50 without departing from the present invention. It should also be understood that the zipper 54 may be replaced with hook and loop fasteners or buttons without departing from the present invention. The cushion 52 is preferably made of an open cell polyurethane foam material which conforms to the patient's waist, thereby providing an abduction pillow effect.

Certain preferred embodiments have been described in order to illustrate the elements of the present invention. Modifications to the disclosed embodiments which do not depart from the invention will be appreciated by persons skilled in the art. Such modifications are intended to be encompassed within the following claims.

I claim:

1. An arm sling comprising:
   a forearm support section having an elbow end portion and a wrist end portion for receiving a patient's forearm, said forearm support section including a bottom panel, an elbow panel, and first and second side panels, said bottom panel being intersected by an opening for permitting a patient's forearm to be flexed therethrough;
   a support strap having first and second end portions coupled to the forearm panel near the elbow end portion and the wrist end portion, respectively, for suspending the forearm support section from the patient's shoulder; and,
   releasable fastener means coupled to the bottom panel for closing said opening.

2. An arm sling as recited in claim 1 wherein said opening extends from a point near the elbow end portion to a point near the wrist end portion so that forearm section remains together at the elbow and wrist ends in the open position.

3. An arm sling as recited in claim 1 wherein the fastener means comprises a zipper.

4. An arm sling as recited in claim 1 wherein the fastener means comprises hook and loop fastener strips.

5. An arm sling comprising:
   a forearm support section for receiving a patient's forearm, said forearm support section including an elbow end portion, a wrist end portion, a bottom panel, an elbow panel, and first and second side panels;
   a support strap having first and second end portions coupled to the forearm panel near the elbow end portion and the wrist end portion, respectively, for suspending the forearm support section from the patient's shoulder;
   a pocket panel secured to said bottom panel intermediate said first and second side panels thereby defining an open pocket for receiving a splint;
   releasable fastener means disposed in the pocket for engaging and retaining a splint; and,
   releasable fastener means disposed in the pocket for engaging and retaining a splint; and,
   a splint having a first end portion received in the pocket and secured therein by the fastener means, and having a second end portion projecting from the forearm support section for providing subjacent support for a patient's hand.

6. An arm as recited in claim 6 wherein the means for retaining the splint comprises hook and loop fastener strips, wherein one of said fastener strips is disposed in said pocket, and the other strip is secured to the splint.

7. An arm sling comprising:
   a forearm support section for receiving a patient's forearm, said forearm support section including an elbow end portion, a wrist end portion, a bottom panel, an elbow panel, and first and second side panels;

a support strap having first and second end portions coupled to the forearm support section near the elbow end portion and the wrist end portion, respectively, for suspending the forearm support section from the patient's shoulder;

a pocket panel secured to one of said side panels intermediate the elbow end portion and the wrist end portion, said pocket panel and side panel enclosing a pocket for receiving a cushion; and, a cushion disposed within said pocket.

8. An arm sling as recited in claim 7, wherein the pocket panel is intersected by an access opening for inserting and removing said cushion, including fastener means secured to said pocket panel for closing said access opening.

9. An arm sling as recited in claim 8 wherein the fastener means comprises hook and loop strips.

10. An arm sling as recited in claim 7 wherein the pad is made of polyurethane foam.

* * * * *